US008764757B1

(12) United States Patent
Tumialan

(10) Patent No.: US 8,764,757 B1
(45) Date of Patent: Jul. 1, 2014

(54) MIS TLIF SYSTEMS AND RELATED METHODS

(71) Applicant: Luis M. Tumialan, Paradise Valley, AZ (US)

(72) Inventor: Luis M. Tumialan, Paradise Valley, AZ (US)

( * ) Notice: Subject to any disclaimer, the term of this patent is extended or adjusted under 35 U.S.C. 154(b) by 0 days.

(21) Appl. No.: 13/756,505

(22) Filed: Jan. 31, 2013

Related U.S. Application Data

(60) Provisional application No. 61/592,839, filed on Jan. 31, 2012.

(51) Int. Cl.
*A61B 17/70* (2006.01)
*A61B 1/32* (2006.01)

(52) U.S. Cl.
USPC ........................................ 606/86 A; 600/210

(58) Field of Classification Search
USPC .................. 606/279, 90, 99, 105, 86 A, 264; 600/201, 210, 215, 219, 231, 232
See application file for complete search history.

(56) References Cited

U.S. PATENT DOCUMENTS 7,473,222 B2 * 1/2009 Dewey et al. ................. 600/210

OTHER PUBLICATIONS

"Mast Quadrant Medial Lateral Blades Procedural Solutions Technique" published at least as early as 2006 by Medtronic Sofamor Danek USA, Inc.
"The Use of the Interfuse, an Innovative Modular Intervertebral Body Fusion Device as a Less Invasive Alternative to the Conventional Bilateral Lumbar Intervertebral Fusion Systems" published at least as early as 2009 by the Department of Neurological Surgery Washington University St. Louis.

* cited by examiner

*Primary Examiner* — Pedro Philogene
*Assistant Examiner* — David Comstock
(74) *Attorney, Agent, or Firm* — Adam R. Stephenson, Ltd.

(57) ABSTRACT

MIS TLIF systems and related methods. Implementations of distractor devices may include a first portion and a second portion where the second portion is slidably coupled over the first portion. A position of the second portion relative to the first portion may be adjustable through contacting a distractor latch coupled to the second portion with a plurality of teeth on a side of the first portion. The first portion may include a first pedicle screw pin on an end of the first portion opposing the second portion. The second portion may include a second pedicle screw pin on an end of the second portion opposing the first portion. The first pedicle screw pin and the second pedicle screw pin may be both configured to couple with a pedicle screw head. A length of the distractor device may be configured to be adjustable through sliding of the first portion.

15 Claims, 17 Drawing Sheets

MIS TLIF SYSTEMS AND RELATED METHODS

CROSS REFERENCE TO RELATED APPLICATIONS

This document claims the benefit of the filing date of U.S. Provisional Patent Application 61/592,839, entitled "MIS TLIF Systems and Related Methods" to Luis Tumialán which was filed on Jan. 31, 2012, (the '839 Application) the disclosure of which is hereby incorporated entirely herein by reference.

BACKGROUND

1. Technical Field

Aspects of this document relate generally to device used in surgical operations, such as spinal surgeries.

2. Background Art

Minimally Invasive Transforaminal Lumbar Interbody Fusion (MIS TLIF) surgeries have been carried out using various conventional techniques and using various conventional surgical systems. An example of a conventional surgical system and technique for performing MIS TLIF can be found in Appendix A of the '839 Application which was previously incorporated entirely herein by reference.

SUMMARY

Implementations of distractor devices may include a first portion and a second portion where the second portion is slidably coupled over the first portion. A position of the second portion relative to the first portion may be adjustable through contacting a distractor latch coupled to the second portion with a plurality of teeth on a side of the first portion. The first portion may include a first pedicle screw pin on an end of the first portion opposing the second portion. The second portion may include a second pedicle screw pin on an end of the second portion opposing the first portion. The first pedicle screw pin and the second pedicle screw pin may be both configured to couple with a pedicle screw head. A length of the distractor device may be configured to be adjustable through sliding of the first portion relative to the second portion.

Implementations of distractor devices may include one, all, or any of the following:

The distractor latch may be biased against the plurality of teeth of the first portion through a spring.

The distractor latch may be coupled to the second portion with a pin and the distractor latch may extend through an opening in the second portion to contact the plurality of teeth.

The first pedicle screw pin and the second pedicle screw pin may extend substantially parallel relative to each other from the same side of the distractor device and at the same angle to a plane formed by the surface of the distractor latch that extends substantially parallel with the second portion.

The first pedicle screw pin and the second pedicle screw pin may extend from the end of the first portion and from the end of the second portion, respectively, on the same side of the distractor device.

The first pedicle screw pin and the second pedicle screw pin may extend from the end of the first portion and from the end of the second portion substantially parallel with the first portion and with the second portion, respectively.

An end of the first pedicle screw pin may face away from the second portion and may be aligned substantially parallel with a portion of the first portion that includes the plurality of teeth and where an end of the second pedicle screw pin may face the first portion.

An end of the first pedicle screw pin and an end of the second pedicle screw pin may face each other and the end of the first pedicle screw pin may face the second portion and the end of the second pedicle screw pin may face the first portion.

Implementations of a distractor device may include a rod and a sleeve where the sleeve is slidably coupled over the rod and the rod includes a plurality of teeth on a side of the rod. A distractor latch may be included coupled to the sleeve and configured to contact the plurality of teeth on the rod. A first pedicle screw pin may be coupled to an end of the rod opposite the sleeve where the first pedicle screw pin is configured to couple with a first pedicle screw head. A second pedicle screw pin may be included which may be coupled to an end of the sleeve opposite the rod where the second pedicle screw pin may be configured to couple with a second pedicle screw head.

Implementations of distractor devices may include one, all, or any of the following:

The distractor latch may be coupled to the sleeve with a pin and the distractor latch may extend through an opening in the sleeve to contact the plurality of teeth.

The first pedicle screw pin and the second pedicle screw pin may extend substantially parallel relative to each other from a same side of the distractor device and at a same angle to a plane formed by a surface of the distractor latch that extends substantially parallel with the sleeve.

The first pedicle screw pin and the second pedicle screw pin may extend from the end of the rod and from the end of the sleeve, respectively, on the same side of the distractor device.

The first pedicle screw pin and the second pedicle screw pin may extend from the end of the rod and from the end of the sleeve substantially parallel with the rod and with the sleeve, respectively.

An end of the first pedicle screw pin may face away from the sleeve and may be aligned substantially parallel with a portion of the rod that includes the plurality of teeth. An end of the second pedicle screw pin may face the rod.

An end of the first pedicle screw pin and an end of the second pedicle screw pin may face each other and the end of the first pedicle screw pin may face the sleeve and the send of the second pedicle screw pin may face the rod.

Implementations of an interbody spacer system may include a first interbody spacer including a pin flange extending from at least a portion of a side of the first interbody spacer. A second interbody spacer may be included that includes a tram in at least a portion of a side of the second interbody spacer. The pin flange of the first interbody spacer may be configured to slidably couple into the tram of the second interbody spacer to slidably couple the first interbody spacer and the second interbody spacer together. The first interbody spacer and second interbody spacer may be configured to fit within a disc space between two spinal vertebrae when the first interbody spacer and the second interbody spacer are slidably coupled together.

Implementations of an interbody spacer system may include one, all, or any of the following:

The pin flange may extend along a majority of the side of the first interbody spacer and the tram may extend along a majority of the side of the second interbody spacer. A width of the tram at a first end of the tram may be wider than a width of the tram at a second end of the tram.

The second interbody spacer may contain three or more compartments where the third compartment is located on an anterior face of the second interbody spacer.

The third compartment may be configured to receive a sponge containing rh-BMP-2 and hold it adjacent to allograft or autograft material placed adjacent to the second interbody spacer.

The third compartment may be formed by coupling a cover over an opening in the anterior face of the second interbody spacer after inserting the sponge containing rh-BMP-2 into the opening.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DESCRIPTION

This disclosure, its aspects and implementations, are not limited to the specific components, assembly procedures or method elements disclosed herein. Many additional components, assembly procedures and/or method elements known in the art consistent with the intended MIS TLIF systems and related methods will become apparent for use with particular implementations from this disclosure. Accordingly, for example, although particular implementations are disclosed, such implementations and implementing components may comprise any shape, size, style, type, model, version, measurement, concentration, material, quantity, method element, step, and/or the like as is known in the art for such MIS TLIF systems and related methods, and implementing components and methods, consistent with the intended operation and methods.

The '839 Application previously incorporated entirely by reference contains disclosure of a wide variety of instruments, assistive devices, interbody devices, and other components that can be utilized when performing MIS TLIF surgeries and will be referred to and in this document at various locations.

Figure 1:
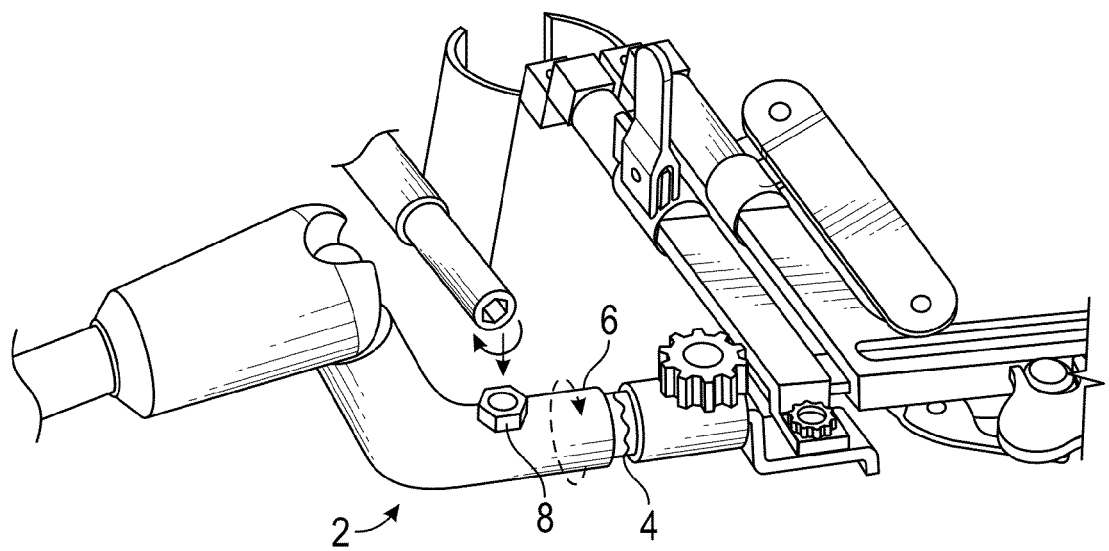
FIG. 1 is a perspective view of an implementation of a retractor arm with rotational capability.

Referring to FIG. 1, an implementation of a retractor arm 2 is disclosed. As illustrated, the retractor arm 2 contains an inserting portion 4 that is inserted into a sleeved portion 6. A set screw is biased against the inserting portion 4 through an opening in the sleeved portion 6 through rotation of nut 8. Implementations of retractor arms 2 that can be rotated through the sleeved portion allow the rotation of the arm 2 and fixing of it through the set screw at a desired angle. This rotational ability of retractor arm allows the surgeon to adjust the angle of the retractor relative to the vertebra over which the retractor is positioned during surgery. Adjustment of the angle may be desirable in a situation where the angle of the entry point for a pedicle screw into the pedicle is lateral to the neural elements and the angle needed for the retractor during decompression and placement of the interbody is medial. Being able to adjust the angle of the retractor to accommodate the pedicle screw insertion and the decompression without adjusting the overall position of the retractor arm can be very helpful, particularly when pedicle screw placement takes place first, followed by decompression and placement of the interbody, followed by placement of the rod, where the angle of the retractors must be adjusted first lateral to medial, then medial to lateral. While this mechanical ability of the retractor arm is useful in MIS TLIF surgeries, it can be used in other minimally invasive procedures as well, such as MIS lumbar laminectomies, where there is a need to angle the refractor medially for contralateral decompression and then angulate to an original neutral position for an ipsilateral decompression.

Figure 2:
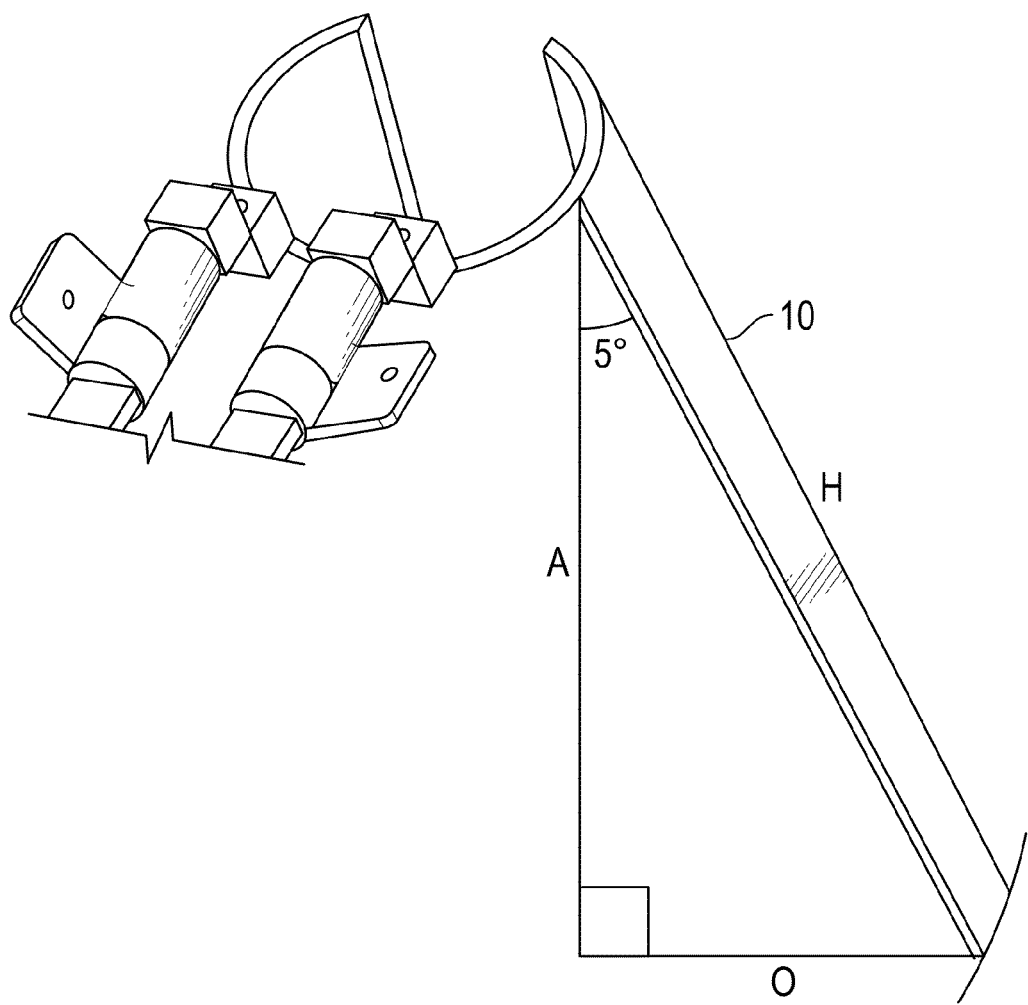
FIG. 2 is a cutaway view of a retractor blade.

During surgery, the blades associated with the retractor (retractor blades) that hold back the surrounding tissue and expose the vertebrae are often angled in the rostral and caudal directions following initial opening of the retractor. This is done to permit additional exposure at depth to allow the surgeon to work without widening the initial opening in the patient's back. At the point in time when the refractor is initially opened and the blades are not angled, the width of the blades is known through use of the measurement markings on the retractor. However, once the blades begin to be angled rostrally and caudally in either of the three present blade angles, the exposure at depth, or the exposure at the bottom of the blades, will be greater or less than the original exposure when the blades were originally not angled, depending on the angle of the blades. The width at depth can be calculated using trigonometry and the sine function with knowledge of the angle at which the particular blade is placed. For instance (and referring to the diagram illustrated in FIG. 2), a retractor opened to a width of 28 mm as determined by the graduated retractor with a 6 cm blade angled to the first angle mark on the rostral blade and with no angle on the caudal blade has an exposure value calculated as the sine of the angle of the blade times the length of the blade plus the total width of the retractor, which would be approximately 5 mm plus 28 mm or 33 mm. If the difference of the exposure and depth value and the exposure shown on the measurement marking were included on a chart for every blade from 4-8 cm and for every angle (there are currently three preset angles in various conventional retractor implementations), the surgeon could quickly ensure that the minimum needed exposure at depth is maintained throughout the surgery as angles on the blades are changed. The charted values of angle depths may then be added to the retractor width shown on the scale on the graduated retractor implementations disclosed in the '839 Application and the total exposure at depth is now known. FIG. 2 is a diagram of this calculation showing the angled blade 10 and the angle exposure value O.

The foregoing discussion indicates that as the blades are angled, the width of the exposure changes. The same geometry that drives the exposure change also indicates that the length of the blade in the perpendicular direction to the refractor arms also decreases as the blade is angled. Because as the blades are angled medially and caudally to increase the exposure at depth following the initial creation of exposure using the blades, the ends of the blades may no longer be directly adjacent the vertebrae as the result of the change in angle. This can be referred to as "creep" where the length of required exposure may exceed the length of the blade after the angling of the blades to the desired angle and exposure value has been accomplished. This situation results from the application of the same geometric principles discussed previously.

Figure 3:
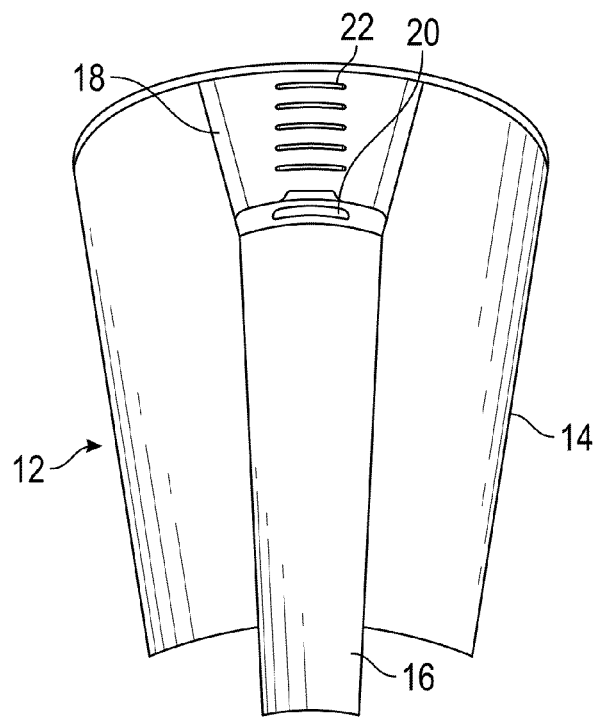
FIG. 3 is a perspective view of a retractor blade with a sleeved extender.

To counter the geometric loss in length of the blade due to medial and caudal angling, altering the structure of the blades to allow them to be lengthened during surgery would assist in eliminating the creep or increasing the exposure. Referring to FIG. 3, in one blade implementation 12, the blade 14 includes a sleeved extender 16 capable of slidably moving within a race 18 in the blade 14. During use, the surgeon would extend the extender 16 beyond the blade edge when increased exposure required the blade to be longer than the existing blade length. As illustrated, the extender 16 may have a groove 20 at one end that can receive an end of an adjuster designed to aid the surgeon in extending the extender at the desired length. One or more grooves 22 may be incorporated in the surface of the blade 14 that engage with a projection or lip extending from the sleeved extender to aid in ensuring the sleeved extender remains at the desired length. In some implementations, actual or scaled measurement markings may be utilized to inform the surgeon of the depth or length of the blade plus the extended portion of the sleeved extender.

In various implementations, the extender 16 may be extended using the same inserter that is used to extend the blades originally. In some implementations, the extender 16 may be automatically extended to a preset value as the blade is angled through use of a mechanical linkage between the refractor arm and the extender 16 that pushes the extender 16 downwardly and outwardly a preset amount as the blade 14 is rotated to a preset angle. In other implementations, the extender 16 may be automatically extended through use of a motor and gearing that is connected to a control circuit that senses the angle of the blade 14 and drives the extender 16 downwardly a corresponding distance to the angle of the blade 14.

Figure 4:
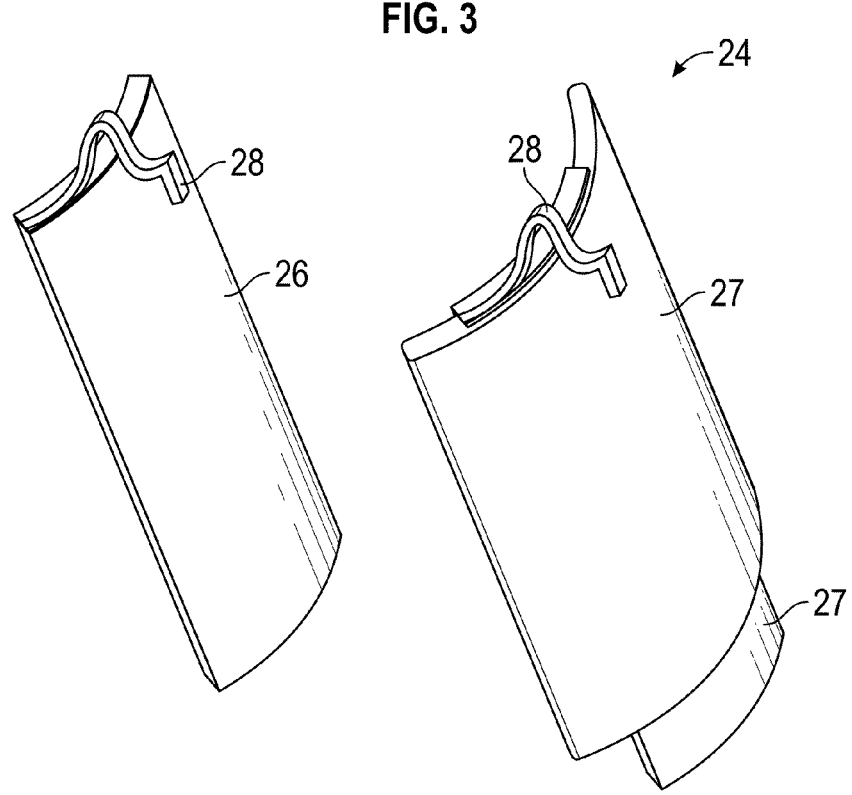
FIG. 4 is a perspective view of a cover slip sleeved extender implementation and a refractor blade.

Referring to FIG. 4, in another blade implementation 14, the length of the blade 24 could be extended through a cover-slip blade extender 26. In these implementations, the cover slip blade 26 would be narrower than the current blade 27 and would slide over the interior side of the blade 27 downwardly until held in place against the blade 27 using a clip 28. Various cover-slip blades of various preset lengths could be included that each correspond to a particular angle value of the retractor. During surgery, the surgeon would select the cover-slip blade needed for the particular retractor blade angle being used and remove it when the angle was changed.

Figure 5:
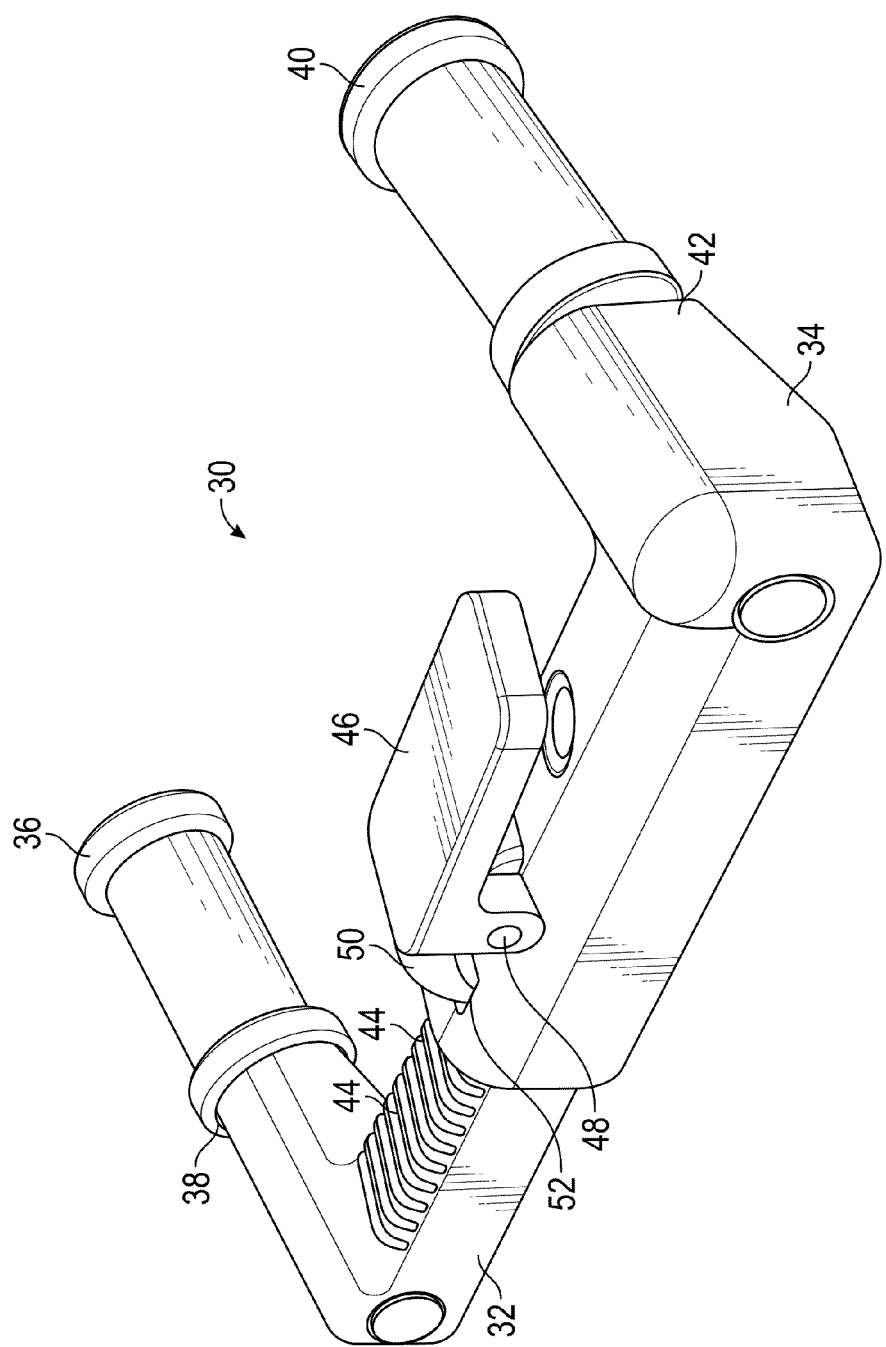
FIG. 5 is a perspective view of a first implementation of a distractor device.

Referring to FIG. 5, an implementation of a distractor device (distractor) 30 is illustrated. The distractor 30 includes a first portion 32 slidably coupled into a second portion 34. A first pedicle screw pin 36 is coupled to the end 38 of the first portion 32 and a second pedicle screw pin 40 is coupled to the end 42 of the second portion 34. The first portion 32 contains a plurality of teeth 44. A distractor latch 46 is coupled to the second portion 34 through a pin 48. In various implementations, the distractor latch 46 is biased using a spring. In various implementations, the distractor latch 46 has a projection 50 that extends through an opening 52 in the second portion 34 and contacts the plurality of teeth 44. The bias force from the spring may press the projection 50 downwardly into a space between two of the plurality of teeth 44. In various implementations, the first and second pedicle screw pins 36, 40 may be coupled to the ends 38, 42 of the first portion 32 and second portion 34, respectively through use of pins, welds, glues, or any other coupling mechanism or may be integrally formed with the first and second portions 32, 34, respectively. In various implementations, a distractor latch may not be used, but a mechanical tightener that operates to fix the one or both of the portions of the distractor together as the tightener is rotated may be utilized (similar to the structures employed with various length-adjusting rods, such as with pool cleaning equipment or tripod legs).

Figure 6:
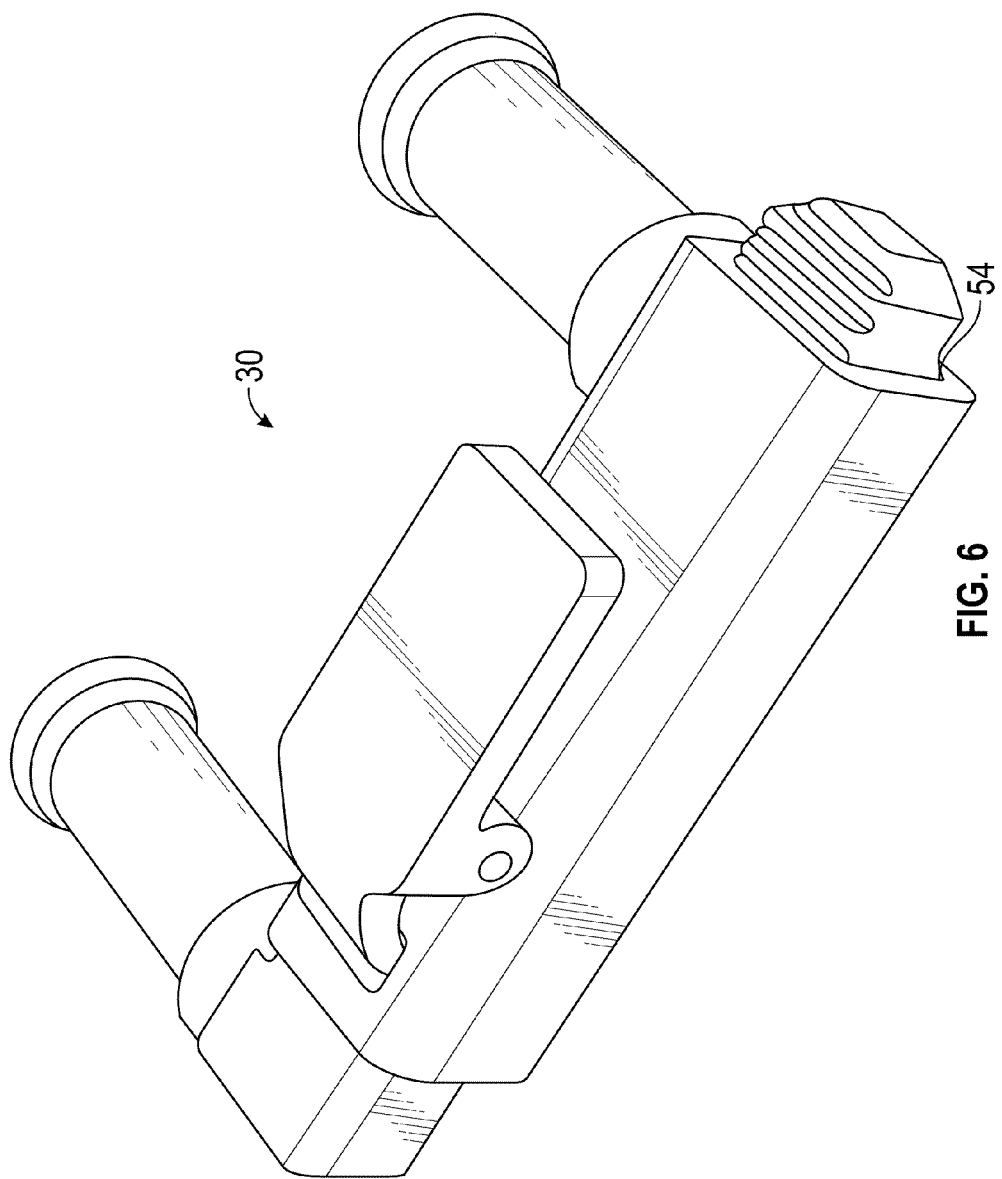
FIG. 6 is a perspective view of the implementation of the distractor device of FIG. 5 in a retracted position.

In various implementations, the first portion 32 may be a rod and the second portion 34 may be a sleeve that is sized to slidably couple over the rod. In various implementations, the first pedicle screw pin 36 and second pedicle screw pin 40 extend substantially parallel from a same side of the distractor (i.e., they both point the same direction from the same side of the distractor). The two pins 36, 40 also are at the same angle to a plane formed by the top flat surface of the distractor latch. This plane is substantially parallel with the second portion. Referring to FIG. 6, in various implementations, a length (longest dimension) of the distractor 30 is varied by slidably moving the sleeve over the rod. As illustrated, the sleeve may have an open end 54 that permits the end of the rod to extend through it when the distractor 30 is in a retracted position (the position the distractor is shown in FIG. 6. In this retracted position, the length of the distractor 30 may at its shortest value.

Figure 7:
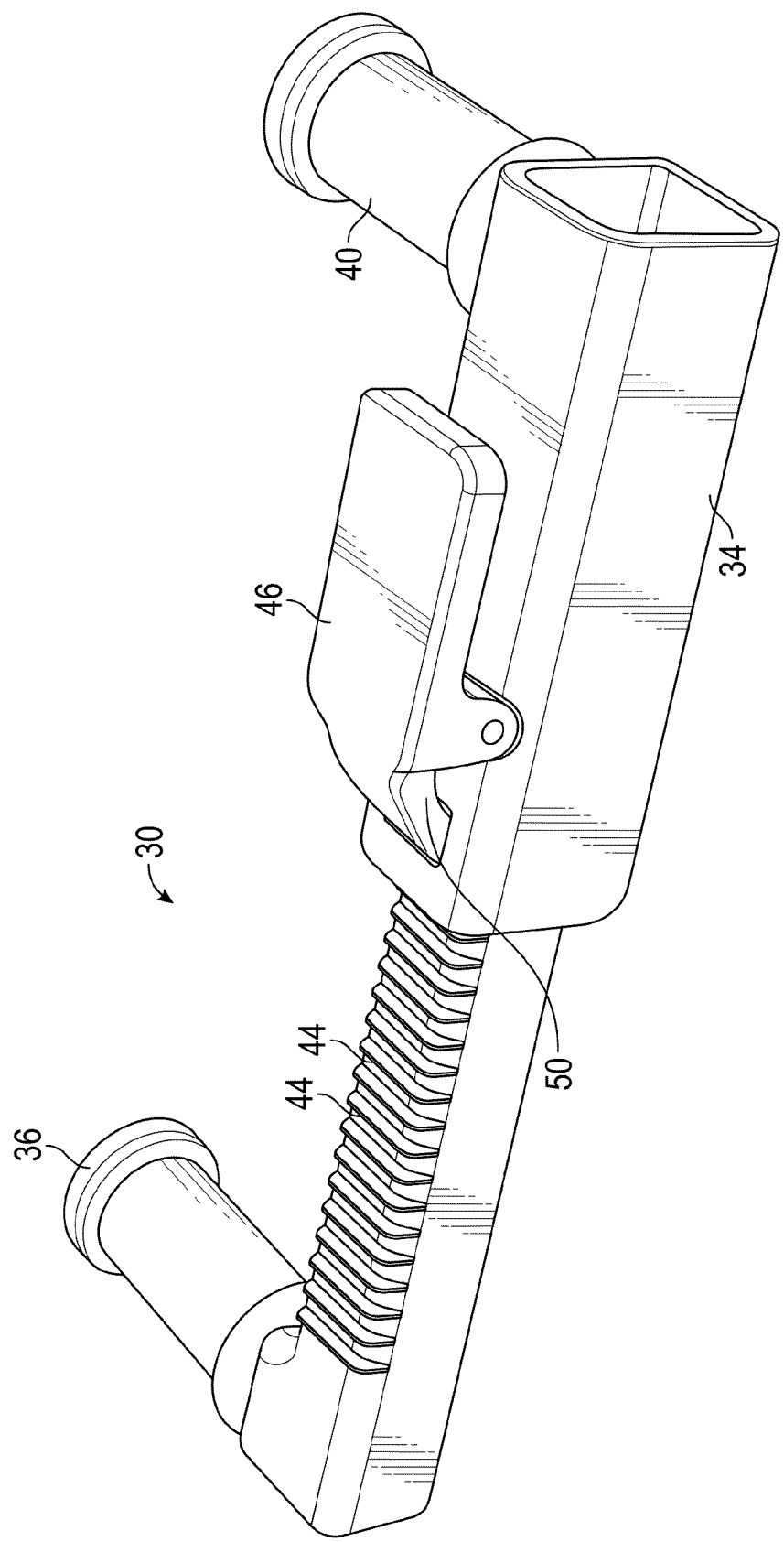
FIG. 7 is a perspective view of the implementation of the distractor device of FIG. 5 in an extended position.

Referring to FIG. 7, the distractor 30 is shown in an extended position. To transition from the retracted position to the extended position, the surgeon may press downward on the distractor latch 46, thereby disengaging the projection 50 from the plurality of teeth 44 and slide the second portion 34 so as to increase the length of the distractor. When the desired length is reached, the surgeon may let go of the distractor latch 46 and reengage the projection 50 with the plurality of teeth as the projection 50 moves downwardly under spring bias force. In various implementations, a spring may not be employed, and the projection 50 may be held in contact at a desired position through the plurality of teeth through gravity force and/or bias forces applied at the ends of the first and second pedicle screw pins 36, 40.

Figure 8:
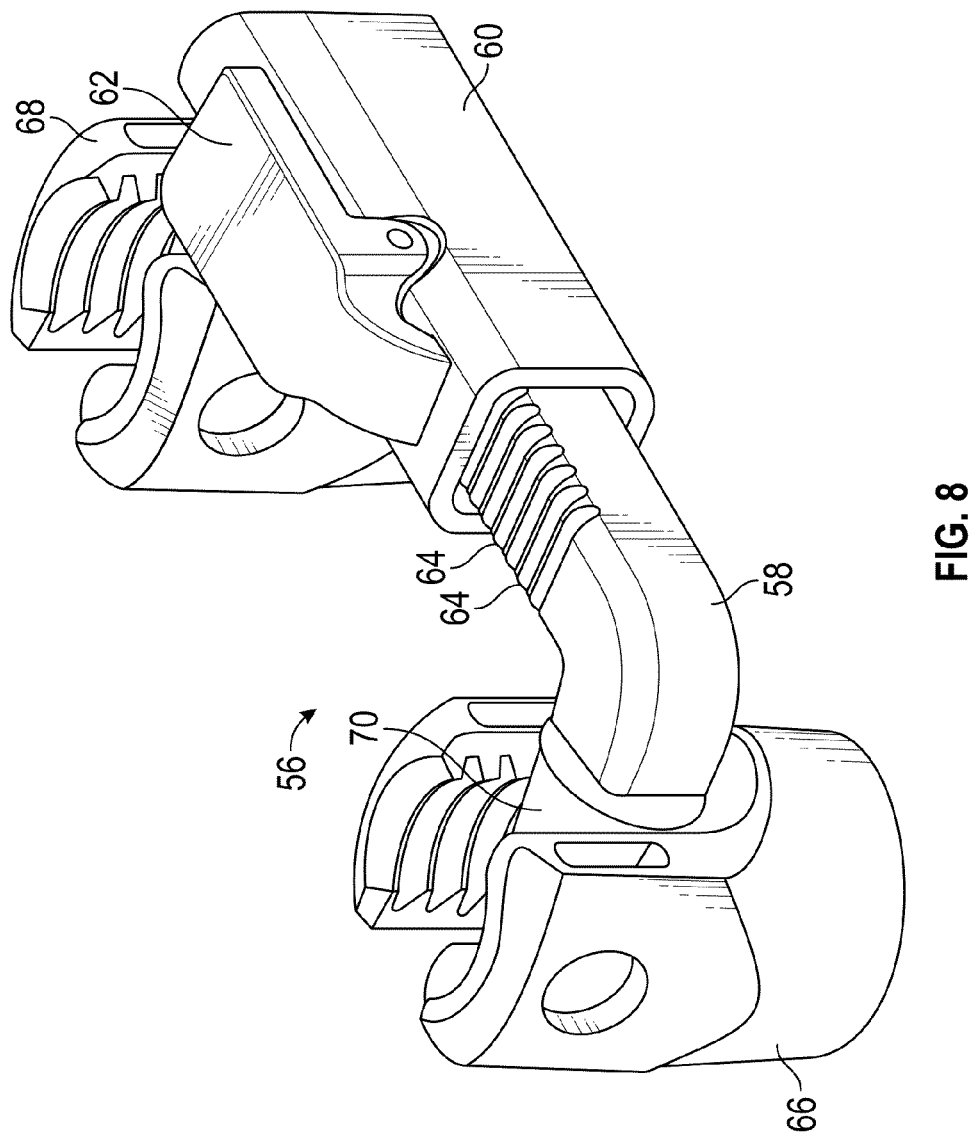
FIG. 8 is a perspective view of a second implementation of a distractor device coupled to two pedicle screw heads.

Referring to FIG. 8, a second implementation of a distractor 56 is illustrated. As illustrated, the distractor 56 includes a first portion 58 (rod) and a second portion 60 (sleeve), and a distractor latch 62 coupled with a plurality of teeth 64. Here, the distractor 56 is illustrated coupled with two pedicle screw heads 66, 68. In this implementation, the first pedicle screw pin 70 and the second pedicle screw pin 72 both extend from the end of the first portion 58 and the an end of the second portion 60 on the same side of the distractor device. Implementations of distractors disclosed herein are used to aid the surgeon in capturing height restoration between two vertebrae during an MIS TLIF operation. These distractors are used during the process of trialing and placing the graft and/or interbody device following discectomy. In an MIS TLIF operation, an ideal interbody device will restores the foraminal height and coronal balance between the two vertebrae. The surgeon typically strives to place the largest and widest graft/interbody device to ensure an optimal environment for fusion and restore the disc space to anatomical height. In certain circumstances, the advanced degeneration present in the patient results in severe disc collapse, which creates a challenging scenario for interbody preparation and graft placement, as the space between the two vertebrae is substantially reduced due to the existing anatomy. Conventionally, provisional rods have been used to hold open the disc space where the provisional rods are placed on the side contralateral to the TLIF. As the disc space is accessed, pedicle screws inserted into the vertebrae, and the height restored by the surgeon, a provisional rod is placed in the pedicle screws and set screws are secured into the heads of the pedicle screws over the provisional rod to hold it in place and capture the height restoration. Since the provisional rod that is placed is seldom the rod that would be ultimately implanted, the work of provisional rod placement and set screw placement is lost and the same task must be repeated when the definitive implanted rod is placed. Furthermore, as the height is restored, often the provisional rod that has been placed becomes too short and needs to be replaced with a longer one, which results in an iterative provisional rod placement process where rods of greater lengths must be inserted and secured with set screws.

The distractor device implementations disclosed herein couple with the pedicle screw heads without the need for use of set screws to couple with the pedicle screw pins. As illustrated in FIG. 8, the pedicle screw pins 70, 72 fit substantially perpendicularly into the set screw openings in the pedicle screw heads 66, 68. Once seated in the pedicle screw heads 66, 68, the distractor 56 permits the surgeon to use the distractor latch 62 to distract, or lengthen and/or shorten the space between the two vertebrae and slidably set the distance between the two vertebrae with the latch and the plurality of teeth 64. Because the length of the distractor 56 is adjustable through the plurality of teeth 64 and the distractor latch 62, the surgeon can adjust the length of the distractor 56 during surgery without having to remove the distractor 56 to do so from the pedicle screw heads 66, 68.

Figure 20:
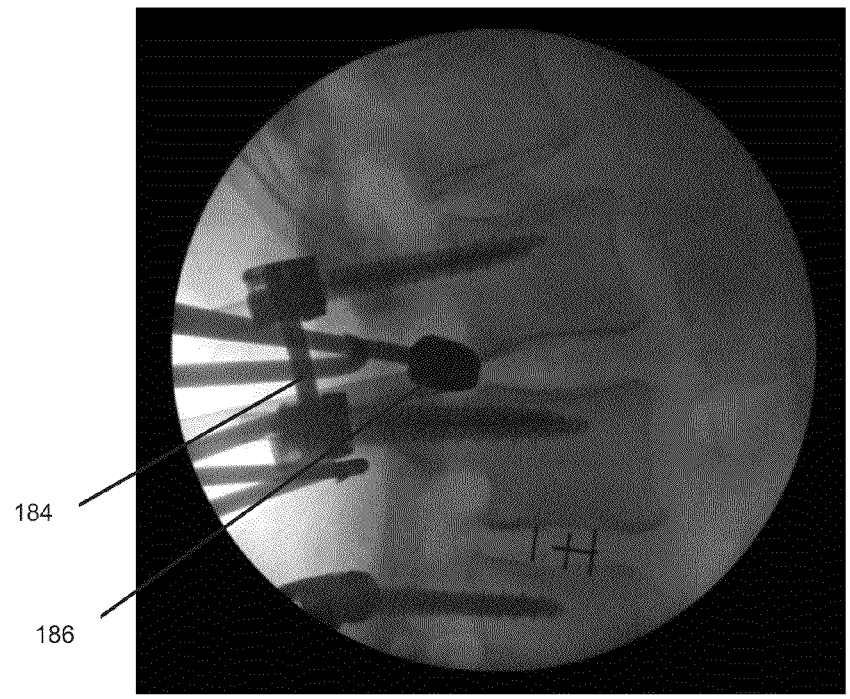
FIG. 20 is an intraoperative fluoroscopic image of a trial attempting to be inserted between two vertebrae.
Figure 21:
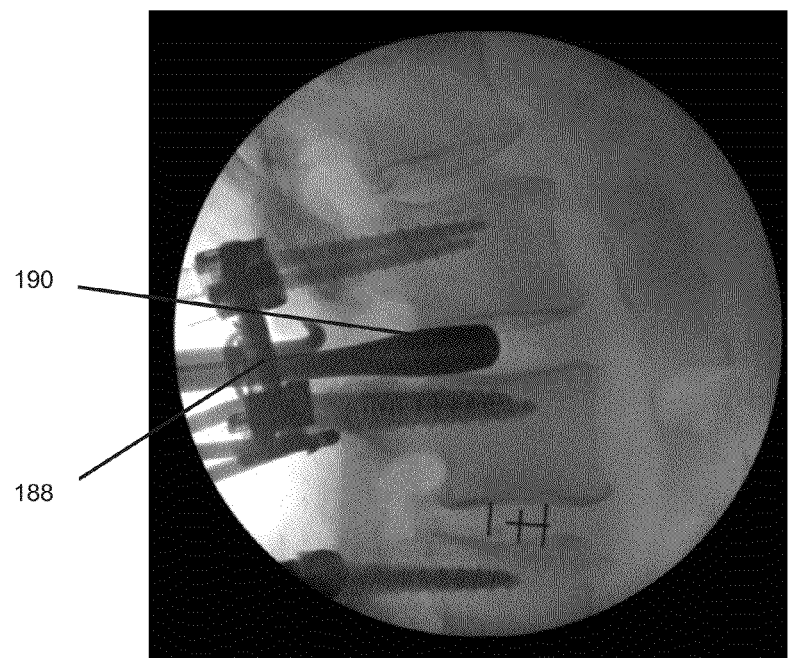
FIG. 21 is an intraoperative fluoroscopic image of a trial being inserted between two vertebrae after separation of the vertebrae using a distractor.
Figure 22:
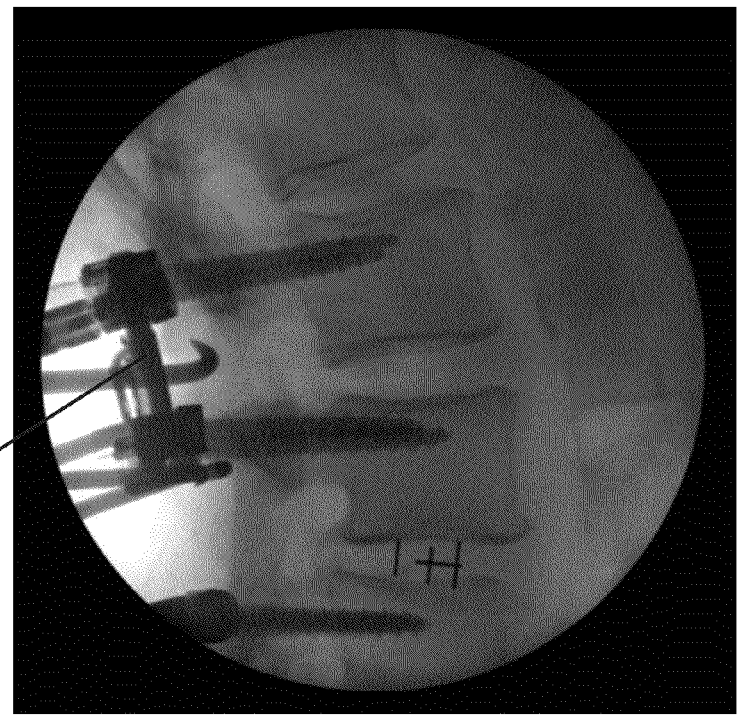
FIG. 22 is an intraoperative fluoroscopic image of the vertebrae after removal of the trial showing the distractor maintaining the space between the vertebrae.
Figure 23:
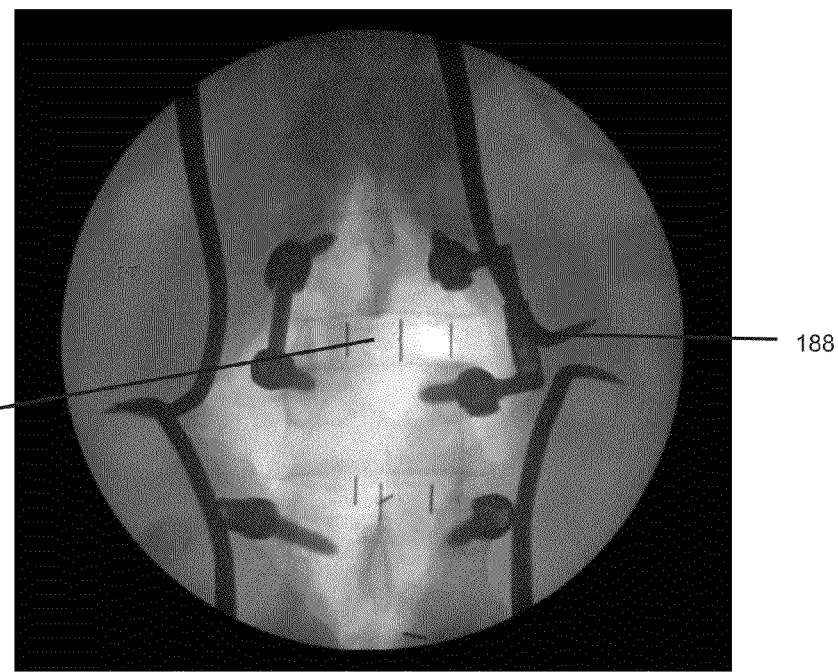
FIG. 23 is an intraoperative fluoroscopic image of the distractor in place after placement of the interbody devices on both levels in a two level MIS TLIF surgery.

Referring to FIG. 20, a lateral intraoperative fluoroscopic image is shown of a provisional rod 184 coupled to two pedicle screws. A trial 186 is also shown which is not able to be inserted between the two vertebrae because the space between the vertebrae has been reduced and is insufficient. Referring to FIG. 21, another lateral intraoperative fluoroscopic image, a distractor 188 is illustrated coupled to the two pedicle screws. The surgeon has used the distractor 188 to distract the two vertebrae, and a larger trial 190 than the trial 186 is now shown inserted between the two vertebrae. The distractor 188 has accordingly enabled the two vertebrae to be spread further apart and has improved the alignment of the two vertebrae relative to each other when compared with the provisional rod. FIG. 22 is a lateral intraoperative fluoroscopic image showing the same vertebrae and distractor 188 with the trial 190 removed. The width of the space between the vertebrae is now maintained solely by the distractor even without the trial 190 present. FIG. 23 is an anterior-posterior (AP) intraoperative fluoroscopic image of the vertebrae shown in FIGS. 20-22 showing the distractor 188 after placement of the second interbody spacer 192. This image demonstrates how the distractor's alignment ensures that the surgeon still has access to the disc space, when compared with the conventional rod on the opposite side of the vertebra.

When conventional provisional rods are used, the position of the rods is contralateral to the interbody access, which may cause the rod to have a limited ability to maintain the height on the side where the TLIF is performed. In these circumstances, it would be ideal for a provisional rod to be used on the side of the interbody access. There are some physical limitations in the capacity to do so in a minimally invasive approach, first because of an inability to place the caudal pedicle screw for pedicle screws systems with a larger pedicle screw profile. In these instances, the caudal pedicle screw is left out on the TLIF side, because it will interfere with access to the disc space. For example, in an L4-5 TLIF from the left, the left L5 pedicle screw is left out until the interbody placement is complete. However, where lower profile pedicle screw systems are employed, the left L5 pedicle screw may be placed with minimal interference for the discectomy and interbody preparation. The second physical limitation that exists with conventional provisional rods is the physical placement of the rod. Even with low profile pedicle screw systems, the placement of a straight rod will block access to the disc space in a minimally invasive approach. Because of this, attempting to use the provisional rod to capture distraction of the vertebrae may be untenable in various situations because the surgeon's access to the disc space is now compromised.

Implementations of distractors like those disclosed in this document may permit the surgeon to continue to have ongoing access to the disc place because the distractor is placed on the lateral side or side of the vertebrae opposite the midline. In these implementations, the distractor maintains the distraction of the vertebrae, but since the distractor is located on the lateral side of the pedicle screw heads, the distractor is not located over the disc space.

Figure 9:
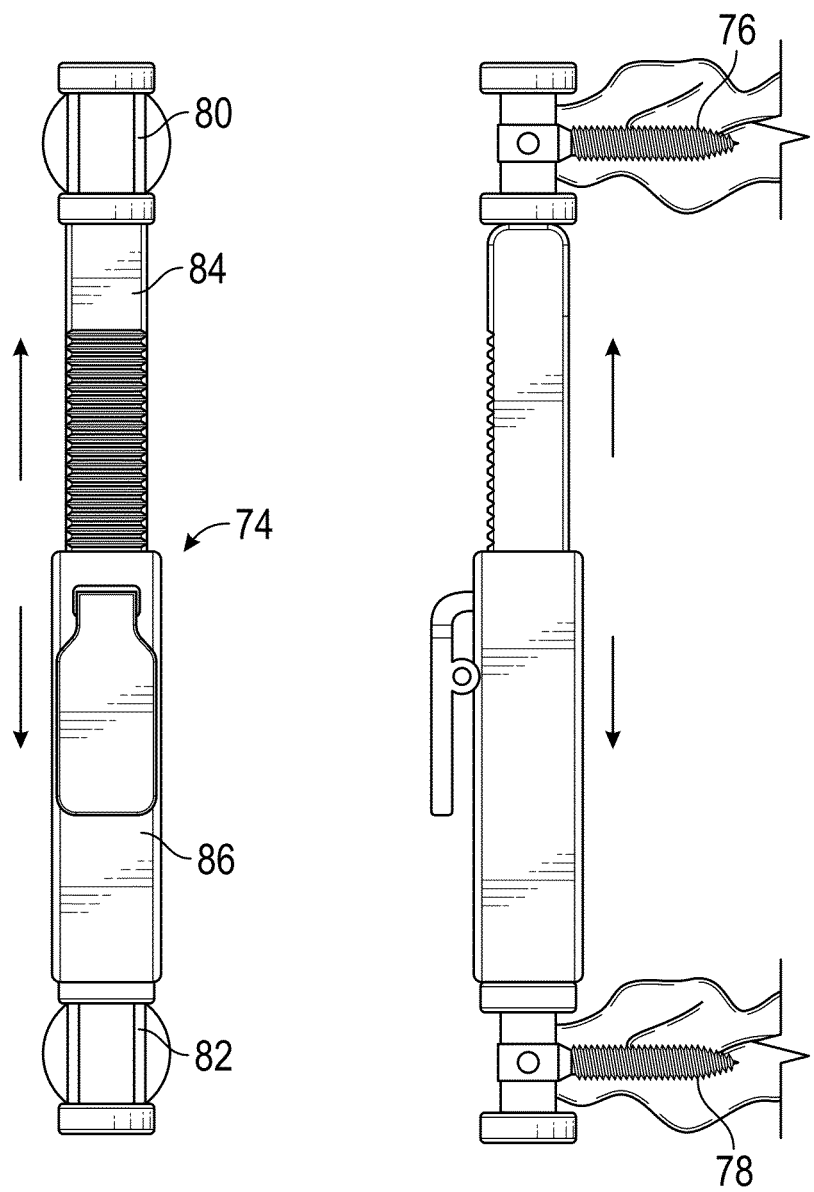
FIG. 9 is a top and side view of a third implementation of a distractor device.

Referring to FIG. 9, an implementation of a distractor 74 is illustrated. As illustrated by the arrows, the distractor 74 is capable of increasing or decreasing its length to accommodate a desired value of distraction between the two vertebrae to which it is coupled through the two pedicle screws 76, 78. In this implementation, the distractor 74 is straight and a line running through the longest dimension of the pedicle screw pins 80, 82 also runs through the rod 84 and sleeve 86 of the distractor 74. The overall shape of this distractor 74 is similar to a conventional provisional rod. Accordingly, this distractor 74 may allow the surgeon to adjust the distraction between the vertebrae, but may block access by the surgeon to the disc space in various situations.

Figure 10:
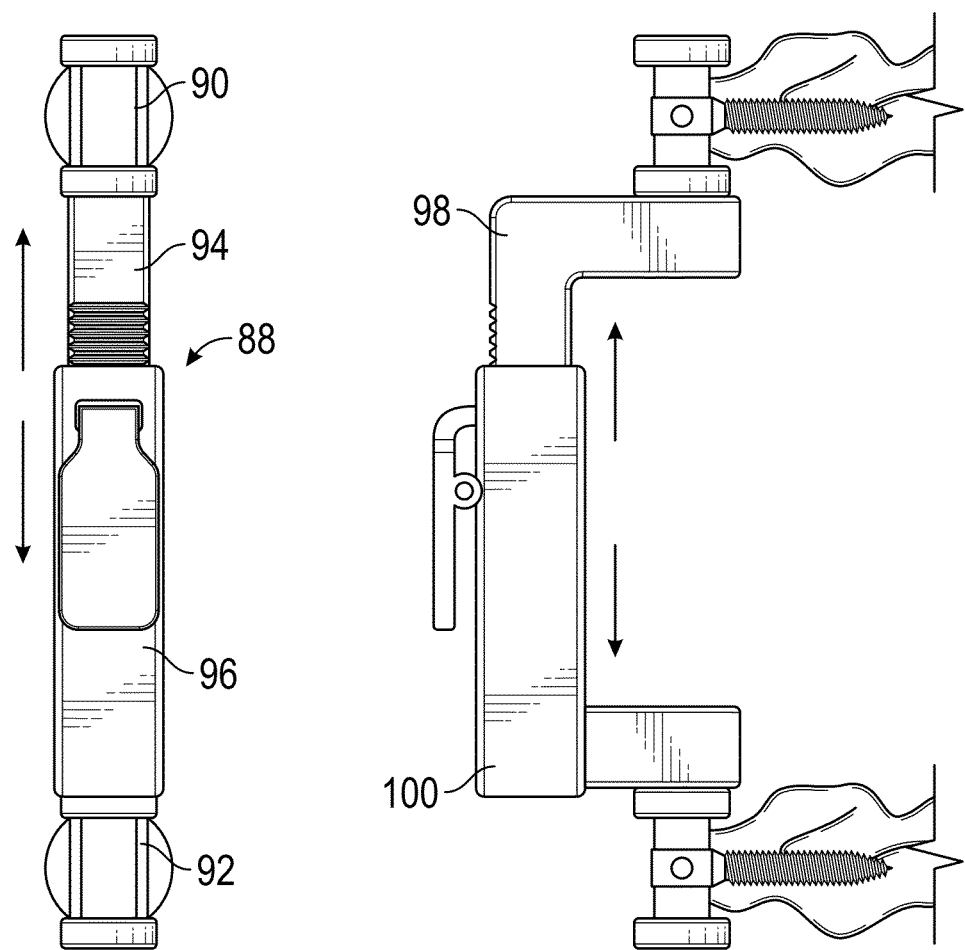
FIG. 10 is a top and side view of a fourth implementation of a distractor device.

Referring to FIG. 10, another implementation of a distractor 88 is illustrated. As illustrated, this distractor functions similarly to the implementation illustrated in FIG. 9. Viewed from the top view illustrated in the left most figure, the distractor 88 likewise is straight and a line running through the longest dimension of the pedicle screw pins 90, 92 also runs through the rod 94, and sleeve 96 of the distractor 88. In the distractor 74 illustrated in FIG. 9 and the distractor illustrated in FIG. 10, the first pedicle screw pins 80, 90 and second pedicle screw pins 82, 92 extend from the end of the rods 84, 94 and sleeves 86, 96 substantially parallel with the rods 84, 94, and the sleeves 86, 96, respectively. However, the rod 94 contains an elbow 98 and the sleeve 96 contains an elbow 100. As illustrated, due to the presence of the elbows 98, 100, rod 94 and the sleeve 96 are offset from the pedicle screw pins 90, 92. In this implementation, because the rod 94 and sleeve 96 are offset, depending upon the angle at which the distractor 88 is coupled into the pedicle screw pins 90, 92, the distractor 88 may not significantly block access by the surgeon to the disc space.

Figure 11:
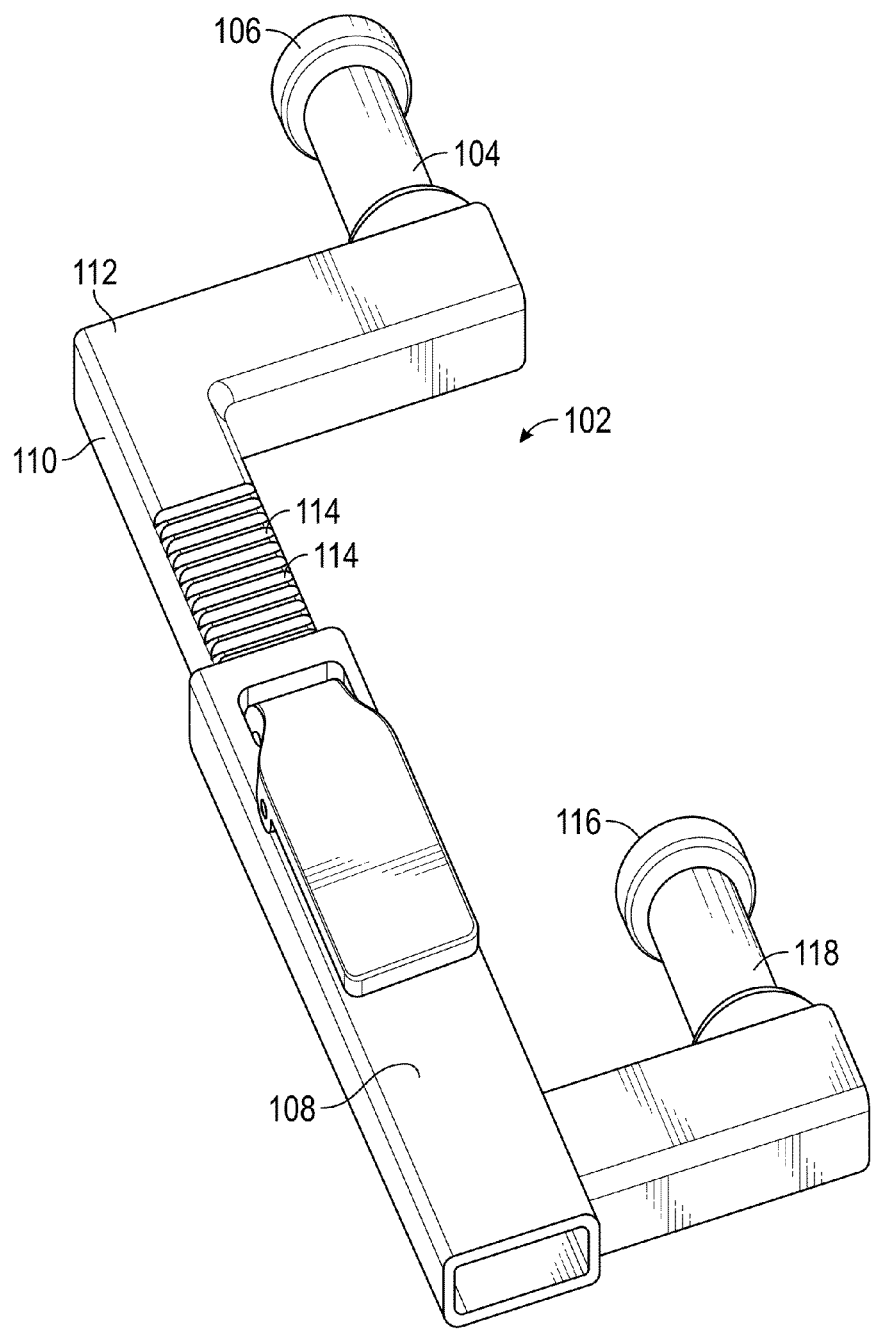
FIG. 11 is a perspective view of a fifth implementation of a distractor device.

Referring to FIG. 11, another implementation of a distractor 102 (J-shaped distractor) is illustrated. As illustrated, the distractor 102 includes a first pedicle screw pin 104 that has an end 106 that faces away from the second portion 108 and is aligned substantially parallel with the portion 110 of the first portion 112 that includes the plurality of teeth 114. An end 116 of the second pedicle screw pin 118 also faces the first portion 112. The second pedicle screw pin 188 and the first pedicle screw pin 104 in this implementation are also aligned substantially parallel. Implementations like those in FIG. 11 allow the distractor 102 to be located away from the disc space as the end of the second portion 108 wraps around the pedicle screw. In various implementations, while the first pedicle screw pin 104, second pedicle screw pin 104, the first portion 112 and second portion 108 are all aligned in substantially the same plane, in various implementations, the first and/or the second portions may be angled toward the vertebrae when the distractor 102 is inserted into the pedicle screws. In these implementations, the first and second portions may be further placed out of the way of the disc space as they are located close to the pedicle screws and/or wrap around them. In these implementations, the structure of the first and/or the second portions may be curved in various ways and the shape of the distractor may also be referred to as J-shaped.

Figure 12:
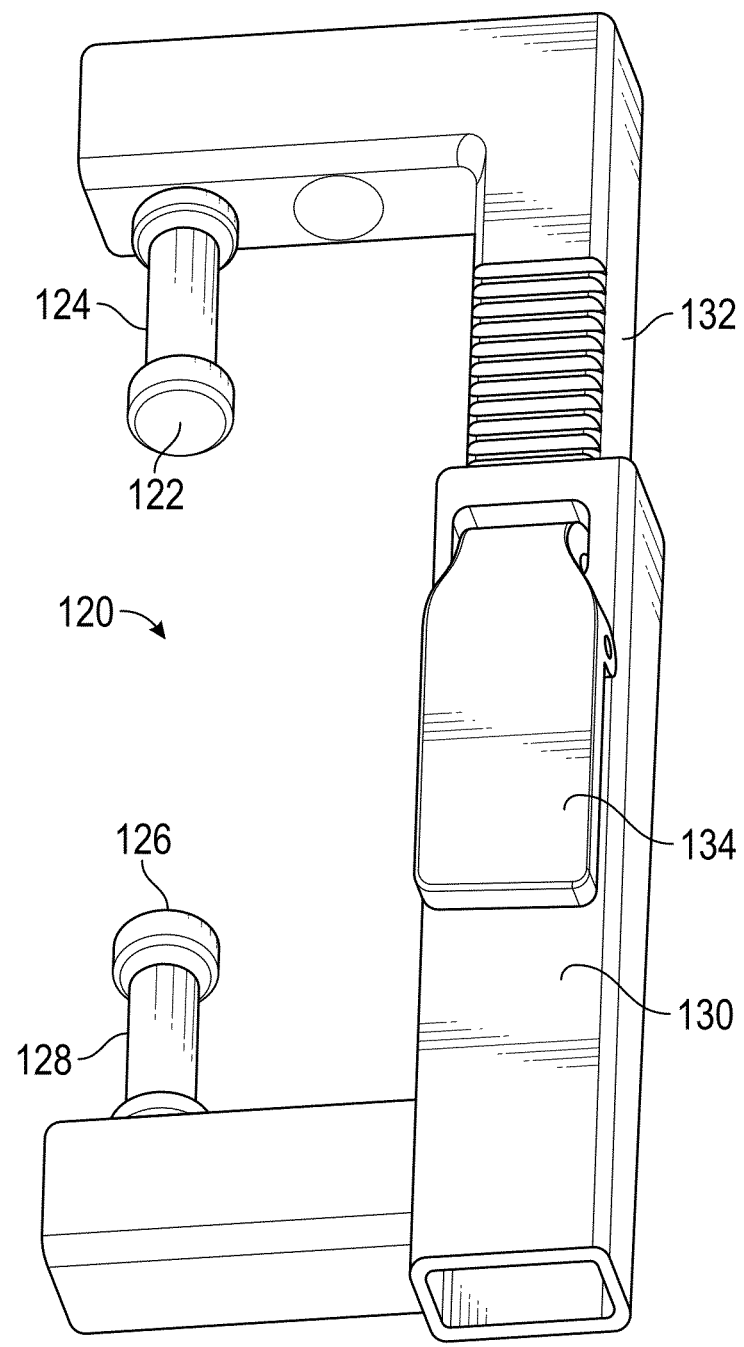
FIG. 12 is a perspective view of a sixth implementation of a distractor device.

Referring to FIG. 12, another implementation of a distractor 120 is illustrated, which may be referred to as a C-shaped distractor. In this implementation, the end 122 of the first pedicle screw pin 124 and the end 126 of the second pedicle screw pin 128 face each other. Also the end 122 of the first pedicle screw pin 124 faces the second portion 130 and the end 126 of the second pedicle screw pin 128 faces the first portion 132. In this implementation, the portion of the distractor 120 that contains the distractor latch 134 is kept out of the way of the disc space by its wrapping around both pedicle screw heads and can be angled toward the vertebrae. Both the C-shaped and J-shaped designs (as well as any of the other distractor implementations disclosed herein) may be used to accomplish ipsilateral provisional distraction.

As the foregoing examples of distractor implementations illustrate, a wide variety of configurations and shapes could be used in various implementations. For example, while the second portions have been illustrated as sleeved and open at the end in most implementations, the distractor 74 illustrated in FIG. 9 has the end of the sleeved second portion 86 closed off so that the second pedicle screw pin 82 can be coupled to the second portion 86. Also, while the various implementations of distractors have used substantially rectangular cross-sections, many other cross-sectional shapes may be utilized in various implementations, such as, by non-limiting example, circular, elliptical, triangular, or any other closed shape. The various distractor implementations may be made of various metals, plastics, or composite materials and may be formed through casting, forming, welding, punching, lathing, molding, injection molding, or any other forming technique adapted to the particular structure to be created and material to be used.

Figure 13:
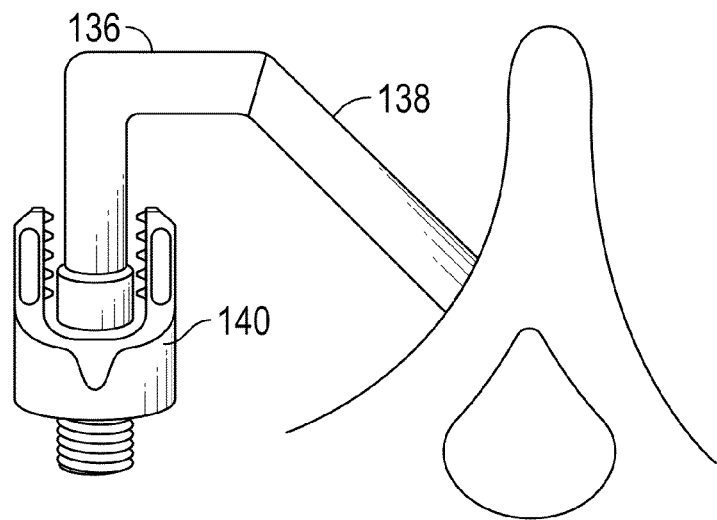
FIG. 13 is a diagram of a medial retractor adjacent to a vertebra.
Figure 14:
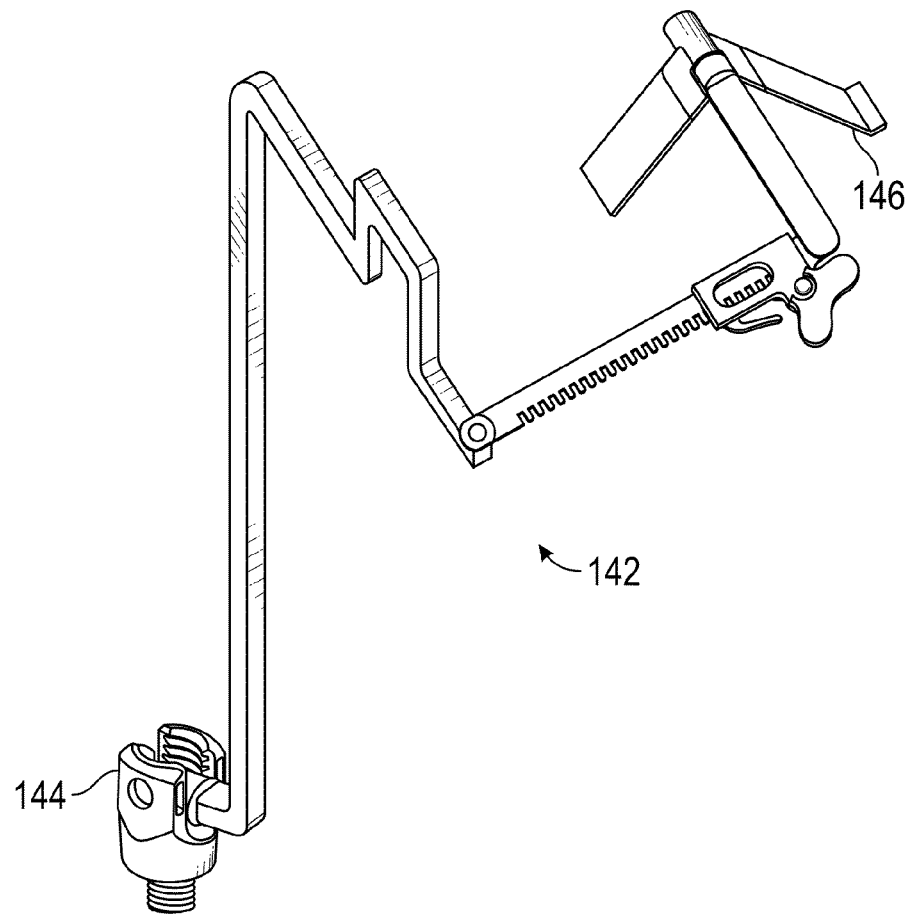
FIG. 14 is a diagram of a medial/lateral retractor implementation coupled to a pedicle screw.

Implementations of MIS TLIF systems like those disclosed herein may also utilize various implementations of medial-lateral retractors. Referring to FIG. 13, a diagram of a cross sectional view of the opening created by a medial-lateral retractor 136 taken perpendicularly to the spreading direction of the retractor blades 138. As can be observed, the medial-lateral retractor 136 is coupled to the pedicle screw 140 on one side, and the remaining blade 138 of the medial-lateral retractor 136 is capable of spreading the opening and angling the opening medially to expose the anatomy sufficiently to allow access to the disc so that a midline decompression of the neural elements can be accomplished. Implementations of medial-lateral retractors disclosed herein may utilize either or both of these aspects, that of being capable of being coupled to the pedicle screw directly or through anchoring with a set screw and the aspect of being able to angulate the medial blade along the vertebra. In addition, various medial-lateral retractor implementations disclosed herein may be coupled directly to any of the distractor implementations disclosed herein through, by non-limiting example, a clip, bracket, latch, screw, pin, or other fastener. Referring to FIG. 14, an implementation of a medial-lateral retractor 142 that incorporates these two aspects, that of coupling to the pedicle screw 144 on the lateral side, and a medial blade 146 that is capable of creating angled medial exposure.

Figure 15:
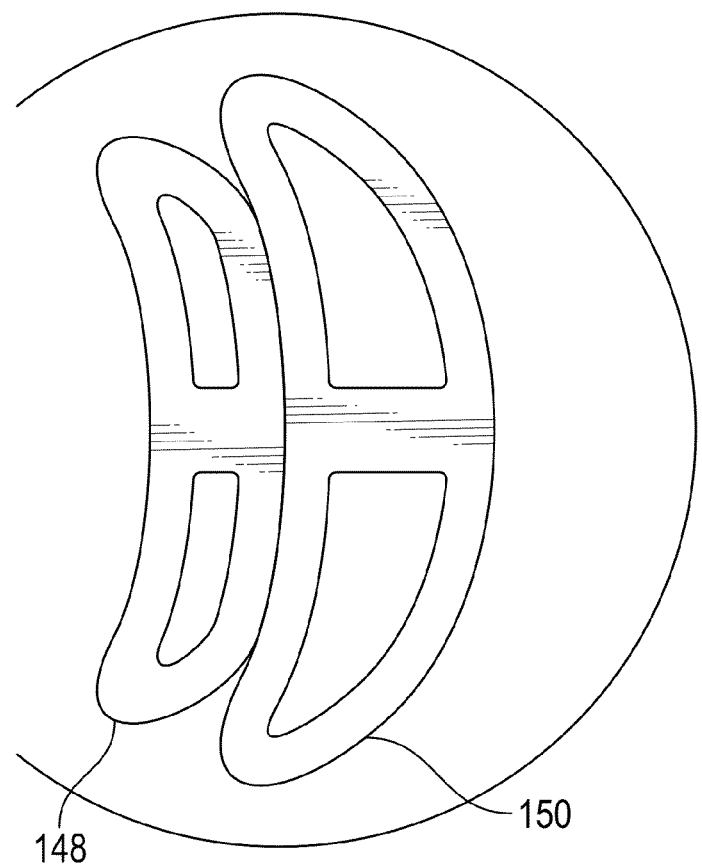
FIG. 15 is a top view of an implementation of nested first and second interbody spacers on top of a vertebra.

Various implementations of MIS TLIF surgical systems and method implementations disclosed herein may utilize various implementations of nested (nestled) interbody spacers. Referring to FIG. 15, a first interbody spacer 148 is shown nested with a second interbody spacer 150 in a top view above the surface of a vertebra. Various conventional interbody spacers can be used in nested configurations, including those marketed under the tradename INTERFUSE by Vertebral Technologies, additional disclosure regarding which is contained in the '839 application. For MIS TLIF surgeries, nesting of conventional spacers marketed under the tradename CRESCENT by Medtronic may be employed to achieve the goals of greater coverage of the interbody devices and increased interbody height. The '839 Application contains disclosure of proof of concept work using such interbody spacers that demonstrate the coverage and interbody height possible with such a configuration. Implementations of nested conventional spacers may ensure lordosis and prevent flat back as well as locking the interbody securely into position without compromising the foramen. In addition, such implementations may reduce the likelihood of migration of the combined nestled spacers.

Figure 16:
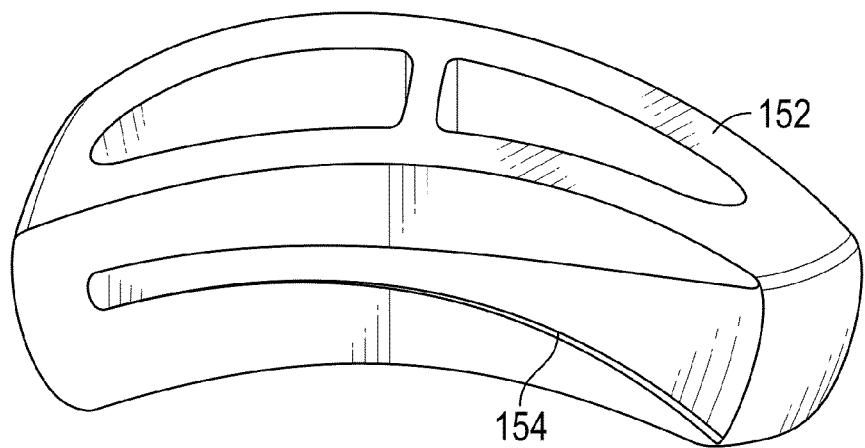
FIG. 16 is a perspective view of an implementation of an interbody spacer showing a tram.
Figure 17:
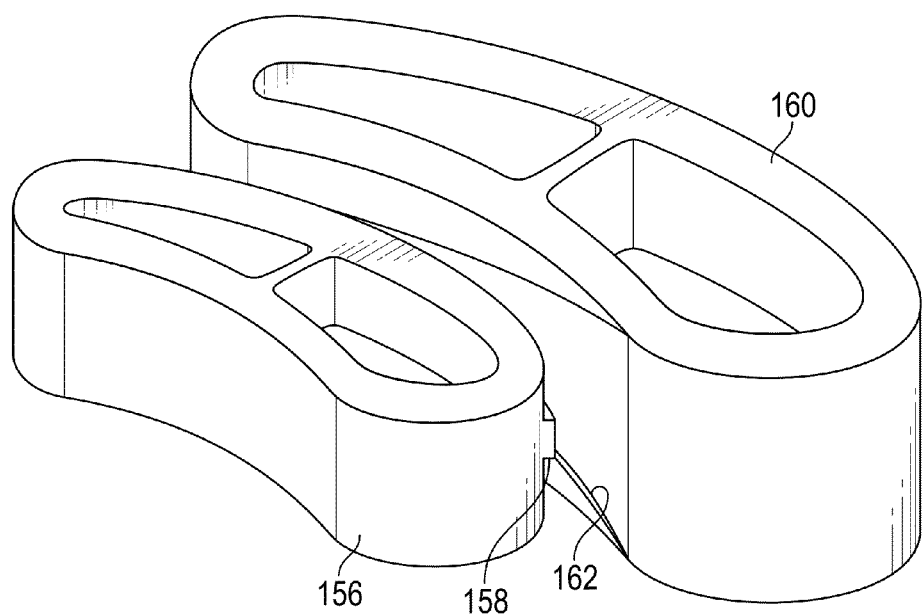
FIG. 17 is a perspective view of implementations of a first interbody spacer and a second interbody spacer.

In situations where nested interbody spacers will be utilized, various implementations of interbody spacers that utilize trams like those disclosed herein may be included to allow them to be sequentially coupled together and inserted into the disc space within the angle allowed during an MIS TLIF surgery (which may be 30 degrees in various situations). Various implementations are detailed in the '839 Application and in this document. Referring to FIG. 16, an interbody spacer 152 with a widened tram 154 to facilitate placement of the second interbody device is illustrated. In some implementations, this tram design may not lock the second interbody device in place to enable removal. In other implementations, the tram design may lock the second interbody device in place to prevent separation of the two interbody devices. Referring to FIG. 17, an implementation of a first interbody spacer 156 containing a pin flange 158 extending from at least a portion of the side of the first interbody spacer 156 is illustrated adjacent to a second interbody spacer 160 that includes a tram 162 in at least a portion of a side of the second interbody spacer 160. Various implementations may have the pin flange 158 and the tram 162 extend along a majority or all of the sides of the first interbody spacer 156 and second interbody spacer 160. The pin flange 158 is sized to slide into the tram 162 and slidably couple to the first interbody spacer 156 and the second interbody spacer 160 together. During use, the surgeon would first insert the second interbody spacer 160 in between the vertebrae, and then would insert the pin flange 158 of the first interbody spacer 156 into the tram 162 and slide the first interbody spacer 156 into the space between the two vertebrae. If the two interbody spacers needed to be removed, the removal process would be the opposite of the insertion process.

Those of skill in the art will readily appreciate that a set of various spacers with trams can be constructed for various desired spacer sizes. Also, any number of interbody spacers could be nested in various configurations, where one or more interbody spacers could have both a pin flange and a tram to enable it to slidably couple two other interbody spacers together.

Figure 18:
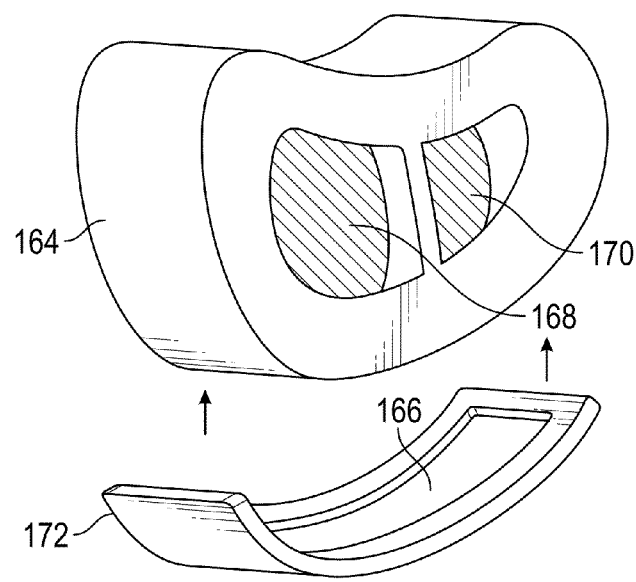
FIG. 18 is a perspective view of an interbody spacer showing a cover.
Figure 19:
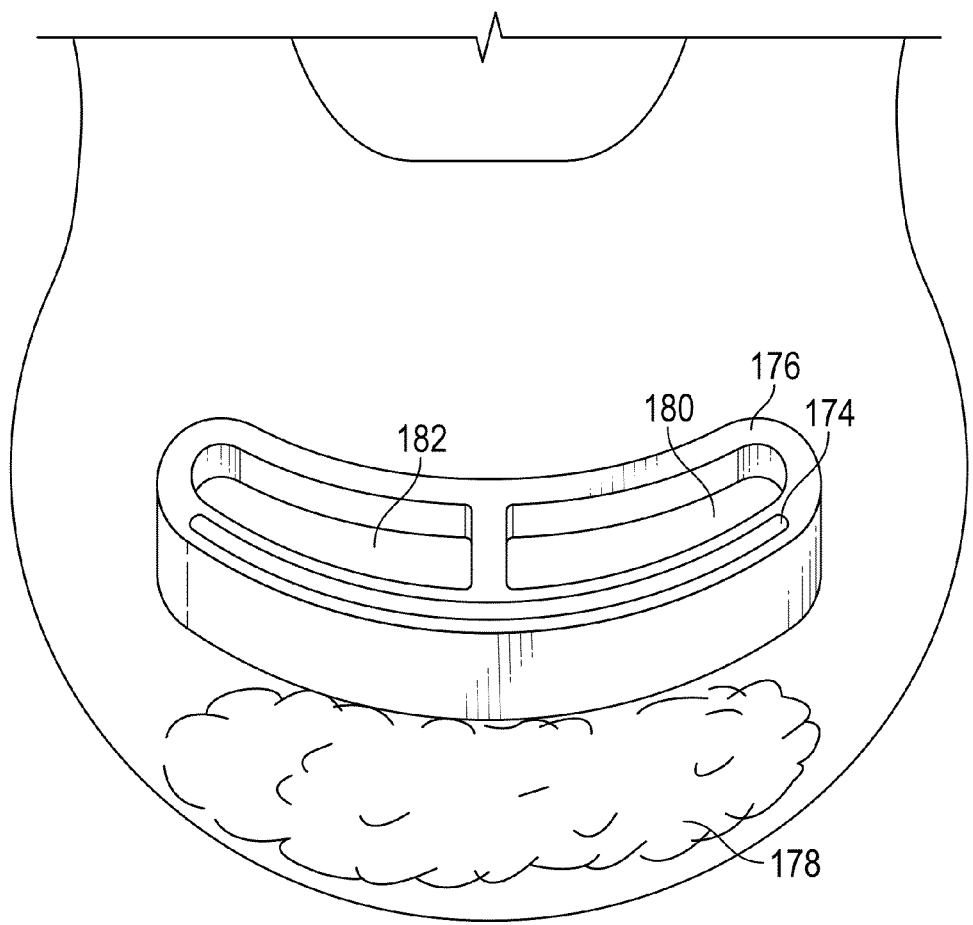
FIG. 19 is a top perspective view of an interbody spacer implementation adjacent to allograft material on a vertebra.

Referring to FIGS. 18 and 19, the various interbody spacer implementations (particularly second interbody spacers) could be modified to contain a compartment for the inclusion of rh-BMP-2. Referring to FIG. 18, an implementation of an interbody spacer 164 containing a third chamber 166 on the anterior aspect of interbody spacer 164 configured to hold a sponge containing rh-BMP-2 is illustrated. As illustrated, the third chamber 166 is formed after the autograft or allograft is placed within the existing two chambers 168, 170 of the interbody spacer 164 by placing a sponge containing rh-BMP-2 on the anterior aspect of the device and a cover 172 being placed over it. In particular implementations, the cover 172 functions as a screen supporting the sponge and places the rh-BMP-2 in the vicinity of the allograft or autograft but away from the neural elements. In particular implementations, about 1.05 mg of rh-BMP-2 may be included. In other implementations, referring to FIG. 18, the cover may contain an opening on one or both of its longest dimensions that leaves an opening 174 on one or both sides of the interbody spacer 176. In these implementations, the cover would not function as a screen. As illustrated in FIG. 19, the allograft/autograft material 178 can be placed in between the vertebrae first, followed by the second interbody spacer 176 with the opening(s) that permit the sponge containing rh-BMP-2 to be made available to the bone. Allograft/autograft material can also be placed in the other two chambers 180, 182.

In implementations of interbody spacers utilizing a third chamber, the sponge size that is selected may be extra-extra small among conventional sponge sizes. The use of the third chamber may prevent issues noted in conventional surgeries due to migration of the small sponge within the existing chambers of conventional large spacers and from compression of the sponge. In addition, the use of the third chamber increases the surgeon's ability to prevent or limit contact of the rh-BMP-2 with the neural elements which may result in minimization of any delayed complications resulting from use of the rh-BMP-2.

In places where the description above refers to particular implementations of retractors, distractor devices, interbody spacers and implementing components, sub-components, methods and sub-methods, it should be readily apparent that a number of modifications may be made without departing from the spirit thereof and that these implementations, implementing components, sub-components, methods and sub-methods may be applied to other retractors, distractor devices, interbody spacers and implementing components.

What is claimed is:

1. A distractor device comprising:
a first portion and a second portion, the second portion slidably coupled over the first portion, a position of the second portion relative to the first portion adjustable through contacting a distractor latch coupled to the second portion with a plurality of teeth on a side of the first portion;
wherein the first portion comprises a first pedicle screw pin on an end of the first portion opposing the second portion;
wherein the second portion comprises a second pedicle screw pin on an end of the second portion opposing the first portion;
wherein the first pedicle screw pin and the second pedicle screw pin are both configured to couple with a pedicle screw head; and
wherein a length of the distractor device is configured to be adjustable through sliding of the first portion relative to the second portion.

2. The device of claim 1, wherein the distractor latch is biased against the plurality of teeth of the first portion through a spring.

3. The device of claim 1, wherein the distractor latch is coupled to the second portion with a pin and wherein the distractor latch extends through an opening in the second portion to contact the plurality of teeth.

4. The device of claim 1, wherein the first pedicle screw pin and the second pedicle screw pin extend substantially parallel relative to each other from a same side of the distractor device and at a same angle to a plane formed by a surface of the distractor latch that extends substantially parallel with the second portion.

5. The device of claim 1, wherein the first pedicle screw pin and the second pedicle screw pin extend from the end of the first portion and from the end of the second portion, respectively, on a same side of the distractor device.

6. The device of claim 1, wherein the first pedicle screw pin and the second pedicle screw pin extend from the end of the first portion and from the end of the second portion substantially parallel with the first portion and with the second portion, respectively.

7. The device of claim 1, wherein an end of the first pedicle screw pin faces away from the second portion and is aligned substantially parallel with a portion of the first portion that comprises the plurality of teeth and wherein an end of the second pedicle screw pin faces the first portion.

8. The device of claim 1, wherein an end of the first pedicle screw pin and an end of the second pedicle screw pin face each other and the end of the first pedicle screw pin faces the second portion and the end of the second pedicle screw pin faces the first portion.

9. A distractor device comprising:
a rod and a sleeve, the sleeve slidably coupled over the rod, the rod comprising a plurality of teeth on a side of the rod;
a distractor latch coupled to the sleeve and configured to contact the plurality of teeth on the rod;
a first pedicle screw pin coupled to an end of the rod opposite the sleeve, the first pedicle screw pin configured to couple with a first pedicle screw head; and
a second pedicle screw pin coupled to an end of the sleeve opposite the rod, the second pedicle screw pin configured to couple with a second pedicle screw head.

10. The device of claim 9, wherein the distractor latch is coupled to the sleeve with a pin and wherein the distractor latch extends through an opening in the sleeve to contact the plurality of teeth.

11. The device of claim 9, wherein the first pedicle screw pin and the second pedicle screw pin extend substantially parallel relative to each other from a same side of the distractor device and at a same angle to a plane formed by a surface of the distractor latch that extends substantially parallel with the sleeve.

12. The device of claim 9, wherein the first pedicle screw pin and the second pedicle screw pin extend from the end of the rod and from the end of the sleeve, respectively, on a same side of the distractor device.

13. The device of claim 9, wherein the first pedicle screw pin and the second pedicle screw pin extend from the end of the rod and from the end of the sleeve substantially parallel with the rod and with the sleeve, respectively.

14. The device of claim 9, wherein an end of the first pedicle screw pin faces away from the sleeve and is aligned substantially parallel with a portion of the rod that comprises the plurality of teeth and wherein an end of the second pedicle screw pin faces the rod.

15. The device of claim 9, wherein an end of the first pedicle screw pin and an end of the second pedicle screw pin face each other and the end of the first pedicle screw pin faces the sleeve and the end of the second pedicle screw pin faces the rod.

* * * * *